US006898459B2

United States Patent
Hayek et al.

(10) Patent No.: US 6,898,459 B2
(45) Date of Patent: May 24, 2005

(54) SYSTEM AND METHOD FOR DIAGNOSING PATHOLOGIC HEART CONDITIONS

(75) Inventors: Carleton S. Hayek, Ellicott City, MD (US); W. Reid Thompson, Baltimore, MD (US); Joseph S. Lombardo, Annapolis, MD (US); Lisa A. Blodgett, Ellicott City, MD (US); Charles B. Cooperman, Highland, MD (US)

(73) Assignee: The Johns Hopkins University, Baltimore, MD (US)

(*) Notice: Subject to any disclaimer, the term of this patent is extended or adjusted under 35 U.S.C. 154(b) by 493 days.

(21) Appl. No.: 10/048,110

(22) PCT Filed: Feb. 23, 2001

(86) PCT No.: PCT/US01/06016

§ 371 (c)(1),
(2), (4) Date: Jan. 25, 2002

(87) PCT Pub. No.: WO01/62152

PCT Pub. Date: Aug. 30, 2001

(65) Prior Publication Data

US 2003/0055352 A1 Mar. 20, 2003

Related U.S. Application Data

(60) Provisional application No. 60/184,375, filed on Feb. 23, 2000.

(51) Int. Cl.[7] ............................................. A61B 5/04
(52) U.S. Cl. ..................................... 600/509; 600/514
(58) Field of Search ............................. 600/509, 513, 600/514, 515, 528

(56) References Cited

U.S. PATENT DOCUMENTS

| | | | |
|---|---|---|---|
| 4,094,308 A | * 6/1978 | Cormier | 600/528 |
| 4,362,164 A | * 12/1982 | Little et al. | 600/382 |
| 4,428,381 A | 1/1984 | Hepp | 600/528 |
| 4,458,693 A | 7/1984 | Badzinski et al. | 600/528 |
| 5,012,815 A | 5/1991 | Bennett, Jr. et al. | 600/528 |
| 5,025,809 A | 6/1991 | Johnson et al. | 600/528 |
| 5,218,969 A | 6/1993 | Bredesen et al. | 600/523 |
| 5,301,679 A | 4/1994 | Taylor | 600/586 |
| 5,687,738 A | 11/1997 | Shapiro et al. | 600/528 |
| 5,957,866 A | 9/1999 | Shapiro et al. | 600/586 |
| 6,050,950 A | 4/2000 | Mohler | 600/485 |
| 6,478,744 B2 | 11/2002 | Mohler | 600/485 |
| 6,480,733 B1 | * 11/2002 | Turcott | 600/516 |
| 6,572,560 B1 | 6/2003 | Watrous et al. | 600/528 |
| 6,629,937 B2 | 10/2003 | Watrous | 600/586 |
| 2002/0052559 A1 | 5/2002 | Watrous | 600/528 |
| 2003/0093003 A1 | 5/2003 | Watrous et al. | 600/528 |

FOREIGN PATENT DOCUMENTS

| | | | | |
|---|---|---|---|---|
| WO | WO 98/20792 | 5/1998 | | A61B/5/02 |
| WO | WO 99/52436 | 10/1999 | | A61B/7/04 |
| WO | WO 02/096293 | 12/2002 | | A61B/7/04 |

* cited by examiner

*Primary Examiner*—Carl Layno
(74) *Attorney, Agent, or Firm*—Francis A. Cooch (57) ABSTRACT

A method of diagnosing pathologic heart conditions in which a time series of heart sounds is filtered and parsed into a sequence of individual heart cycles. A systolic interval as well as systolic sub-intervals are identified for each heart cycle. An energy value is computed for the systolic sub-interval of one or more heart cycles. The energy value computed is proportional to the energy level associated with the filtered series of heart sounds. A composite energy value is then computed for the systolic sub-intervals of one or more heart cycles and compared to a threshold level in order to distinguish between a normal heart and a pathologic heart. The system corresponding to the method is comprised of a portable computing device that manages data collection and stores data collected from new patients, and analyzes data.

23 Claims, 6 Drawing Sheets

SYSTEM AND METHOD FOR DIAGNOSING PATHOLOGIC HEART CONDITIONS

CROSS-REFERENCE TO RELATED APPLICATIONS

This application claims the benefit of International Application No. PCT/US01/06016, filed Feb. 23, 2001 which claims the benefit of prior filed co-pending U.S. Provisional Patent Application No. 60/184,375, filed on Feb. 23, 2000.

STATEMENT OF GOVERNMENT INTEREST

This invention was made with Government support under Contract No. DAMD17-97-7016 awarded by the Department of the Army. The Government has certain rights in the invention.

BACKGROUND OF THE INVENTION

The present invention relates to a system and method for diagnosing pathologic heart conditions based upon heart sound data.

Studies have shown that primary care physicians frequently refer patients to cardiac specialists on the basis of suspicious heart sounds detected by traditional stethoscope auscultation, though a large percentage of these referrals are dismissed by cardiologists as having no pathologic condition. The costs, delays, worry, and administrative burden resulting from these needless referrals could be reduced if the cues that the specialist uses could be incorporated into an algorithm to automatically screen for pathologic heart sounds and murmurs. Although attempts have been made to automate screening by auscultation, no device is currently available to fulfill this function. Multiple indicators of pathology are nonetheless available from heart sounds and can be elicited using certain signal processing techniques such as time-frequency analysis. At least one signal of pathology, the systolic murmur, can reliably be detected and classified as pathologic using a portable electrocardiogram and heart sound measurement unit combined with a time-frequency based algorithm. Time-frequency decomposition analysis holds promise for extending these results to detection and evaluation of other audible pathologic indicators.

In addition, an automatic screening algorithm would be useful for detecting pathologic heart murmurs in settings where a trained professional is not always available, such as pre sports participation physicals, and examinations performed in remote or underserved areas. Furthermore, automated analysis of digitized clinical information such as heart sounds could have major implications for health care delivery systems using telemedicine.

SUMMARY OF THE INVENTION

The present invention comprises a time-frequency murmur diagnostic device and method. The present invention combines a cardiologist's auscultation expertise, a large and growing set of comprehensive heart sound files, and digital signal processing algorithms.

A method of diagnosing pathologic heart conditions in which a time series of heart sounds is filtered and parsed into a sequence of individual heart cycles. A systolic interval as well as systolic sub-intervals are identified for each heart cycle. An energy value is computed for the systolic sub-interval of one or more heart cycles. The energy value computed is proportional to the energy level associated with the filtered series of heart sounds. A composite energy value is then computed for the systolic sub-intervals of one or more heart cycles and compared to a threshold level in order to distinguish between a, normal heart and a pathologic heart.

The system for diagnosing pathologic heart conditions is comprised of a portable computing device that manages data collection and stores data collected from new patients, and analyzes data. Also included is a patient data collection unit, communicable with the portable computing device, for acquiring and digitizing electro-cardiogram (ECG) and heart sound data from a patient. The patient data collection unit is comprised of a pair of transducer contact microphones (primary and reference) for obtaining acoustic data. Also included is a pair of acoustic pre-amplifiers connected with the transducers. The pre-amplifiers have a passband of 20 Hz to 2 kHz and are used to condition acoustic data received from the contact microphones. Variable amplifiers connected with the acoustic pre-amplifiers variably amplify the conditioned acoustic data. Moreover, several electrocardiogram (ECG) electrodes connected to an ECG amplifier record ECG data. The acoustic and the ECG data are passed to an analog to digital converter connected with the variable amplifiers and the ECG amplifier. The data is digitized and sent to the computing device for processing by a screening algorithm implemented by the steps described in the method above.

DESCRIPTION OF THE PREFERRED EMBODIMENTS

Before describing the present invention it is helpful to have a basis for the detection of pathological heart conditions. Analysis of a variety of heart sounds and corresponding diagnoses from the Johns Hopkins School of Medicine (JHU/SOM) has shown that time-frequency analysis is a versatile technique for detecting and classifying pathologic heart conditions. Of the available time-frequency techniques, wavelets are a useful method for representing heart sound frequency dynamics without creating cross term artifacts. Wavelet transforms can be computed for a continuous or discrete set of transform variables, depending on the priority for compactness (e.g., data compression applications) or ease of visual interpretation (e.g., pattern recognition applications), respectively. While compressibility is of interest for future applications, the relative ease of interpretation provided by continuous wavelet transforms (CWTs) suggested their use with the present invention. While wavelet transform analysis are illustrated herein as a preferred method for analyzing heart sound data, Fourier transform analysis may also be implemented by one of ordinary skill in the art in order to analyze heart sound data.

The CWT of a time series, f(t), is defined as:

$$W(a, b) \equiv \int_{-\infty}^{\infty} f(t) \frac{1}{\sqrt{|a|}} \psi^*\left(\frac{t-b}{a}\right) dt \quad \text{(Equation 1)}$$

where f and ψ are both square-integrable, a is a time scaling variable, and b is a time translation variable. This can also be written as a convolution:

$$W(a, b) = f(b) * \psi^*_{a,0}(-b)$$

where $$\psi_{a,b}(t) \equiv \frac{1}{\sqrt{|a|}} \psi\left(\frac{t-b}{a}\right)$$

While it is possible to construct a ψ to yield an optimal peak (compact, high amplitude) in W for a given f, it would not be guaranteed to be optimal for a different time series g. Since the present invention is to be applied to a variety of heart sound signals, a custom wavelet was not implemented. Rather, the alternative was to draw ψ from a pool of wavelets designed to have various advantageous properties. Wavelet transformations known as second order "coiflets" were implemented with the present invention. It is important to note, however, that other wavelet transformations, including custom wavelets, may be implemented without departing from the spirit or scope of the present invention.

Figure 1:
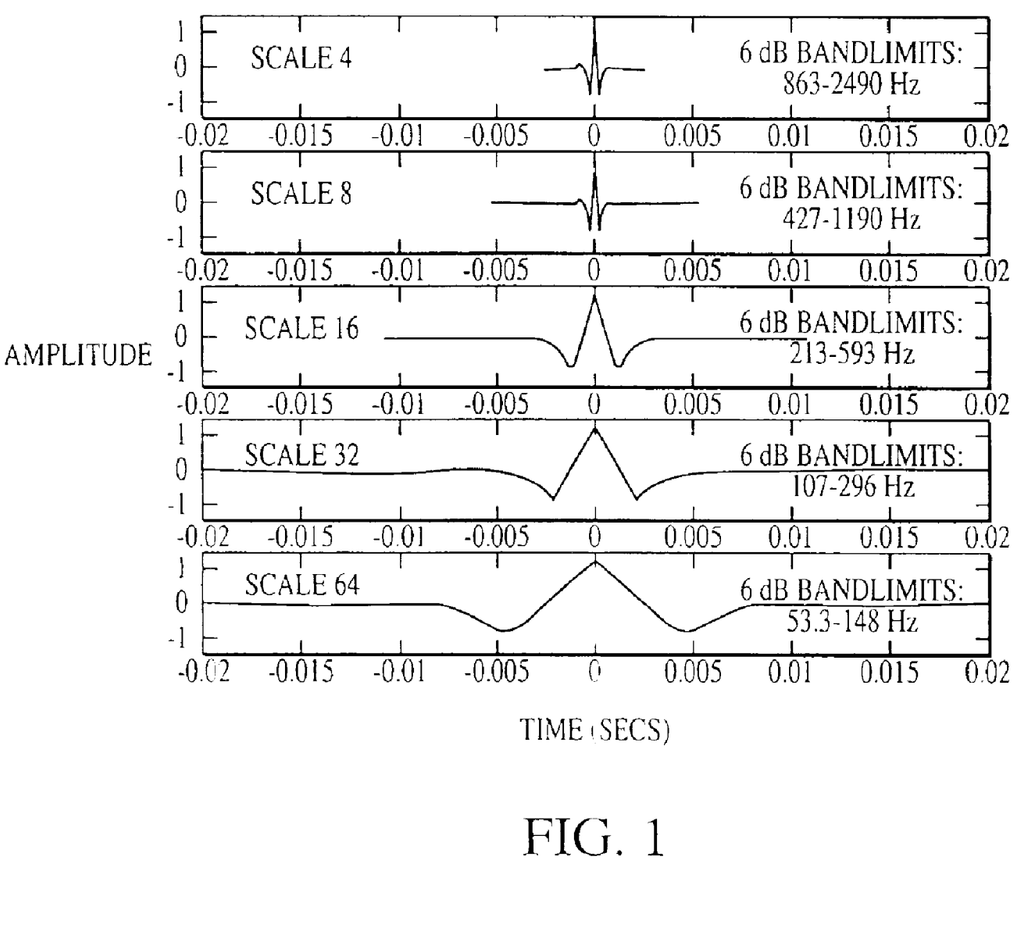
FIG. 1 illustrates a plot of time-frequency analysis basis functions (wavelets) at various scales $\alpha$.

Coiflets of order 2 at various scales, α, are plotted in FIG. 1. The frequency bandpass limits at each scale are given. Due to the equivalence of convolution in the time domain and multiplication in the frequency domain equation 1 shows that the Fourier transform of ψ will act as a bandpass filter of the signal f. The bandpass limits in FIG. 1 are the 6 dB passband frequency limits of the Fourier transform of φ. Wavelets are constructed so as to maintain a constant ratio of center frequency to 3 dB bandwidth (Q), and have a finite duration. Their time-frequency resolution is inherent in their design and scale parameters. This is in contrast to Fourier decomposition, which uses the infinite time extent sine and cosine functions. Time resolution is not inherent in the Fourier transform, but is introduced by the user via windowing the data. Multiple Fourier transforms using distinct window intervals would be required to produce the constant Q decomposition offered by wavelets.

Figure 2:
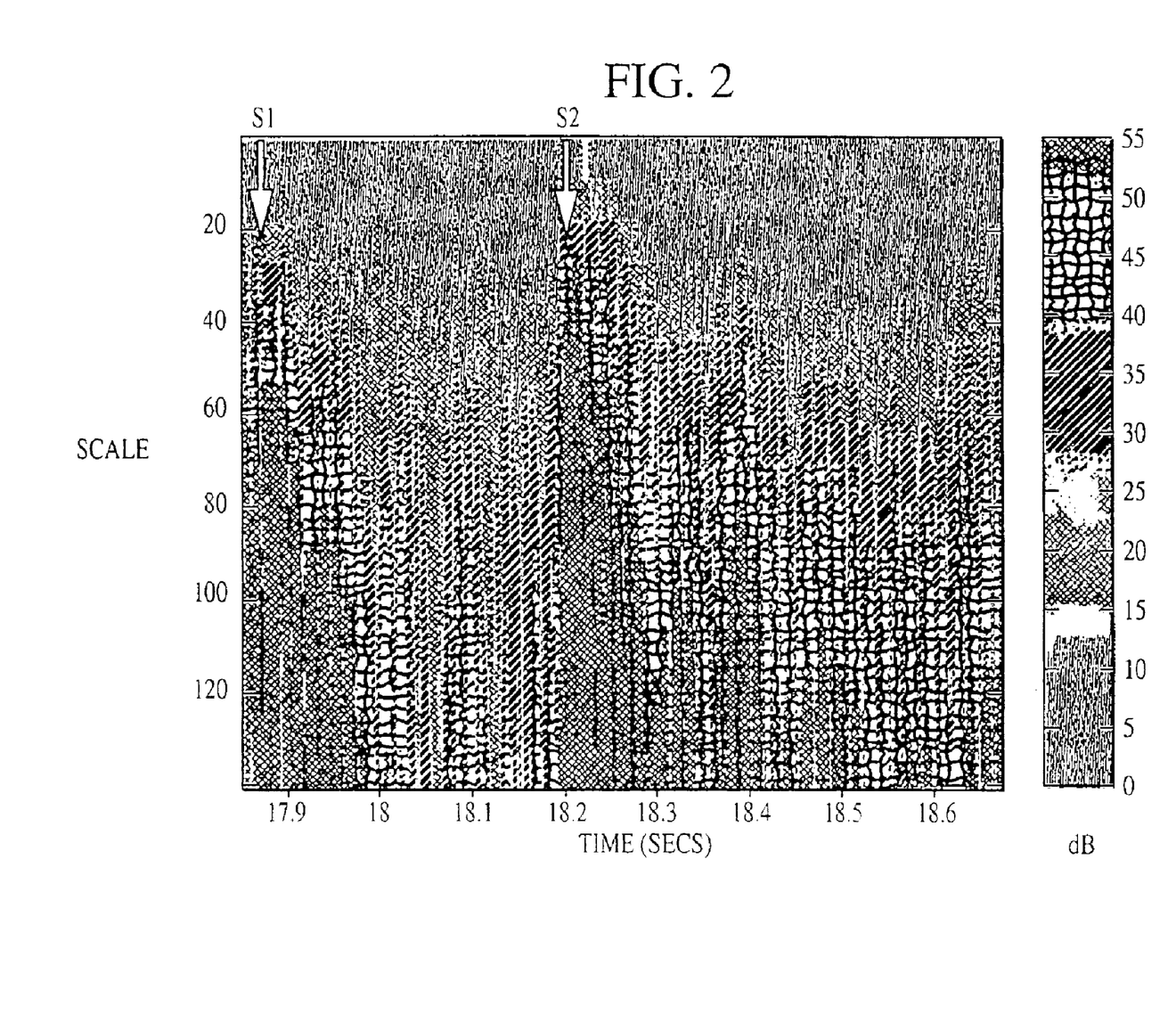
FIG. 2 illustrates a normal heart sound under time-frequency analysis.
Figure 3:
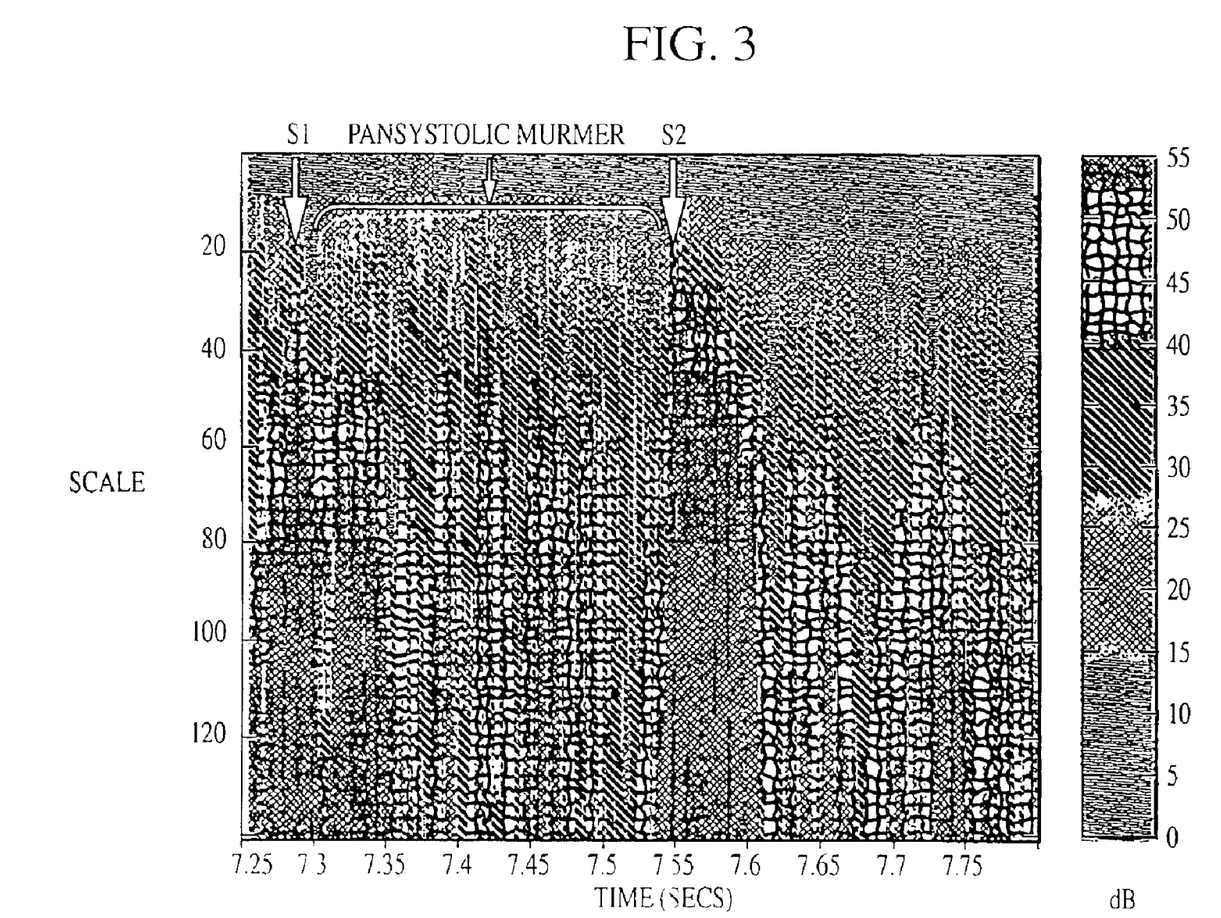
FIG. 3 illustrates a pathologic systolic heart murmur under time-frequency analysis.

Example cases of a normal heart sound and a pathologic systolic heart murmur under wavelet transformation with coiflets are given in FIGS. 2 and 3. These figures demonstrate the clear relationship between an audio-based physician's description used in auscultation and the visual presentation in time-frequency space. A "harsh pan-systolic murmur" is a diffuse area of broadscale (i.e., broadband) energy between S1 and S2. The broadband nature of the sound, which lasts throughout systole, is responsible for "harshness." This straightforward representation of a pathologic indicator in time-scale space is a promising basis for pattern recognition.

Auscultation of pathologic murmurs is keyed to the following observations, according to a study of 222 consecutive patients referred to the Johns Hopkins Pediatric Cardiology clinic:

a. pan-systolic nature of the murmur;
 b. intensity of the murmur>grade 3;
 c. point of maximal murmur intensity at the left upper sternal border (LUSB);
 d. harsh quality of the murmur;
 e. presence of an early or mid-systolic click; or, presence of an abnormal second heart sound.

The goal was to identify systolic murmurs that are indicative of heart defects, and exhibited one or more of the qualities (a)–(d) above. Algorithms may also be implemented to detect heart clicks, and split and abnormal S2 sounds for greater diagnostic utility.

Figure 4:
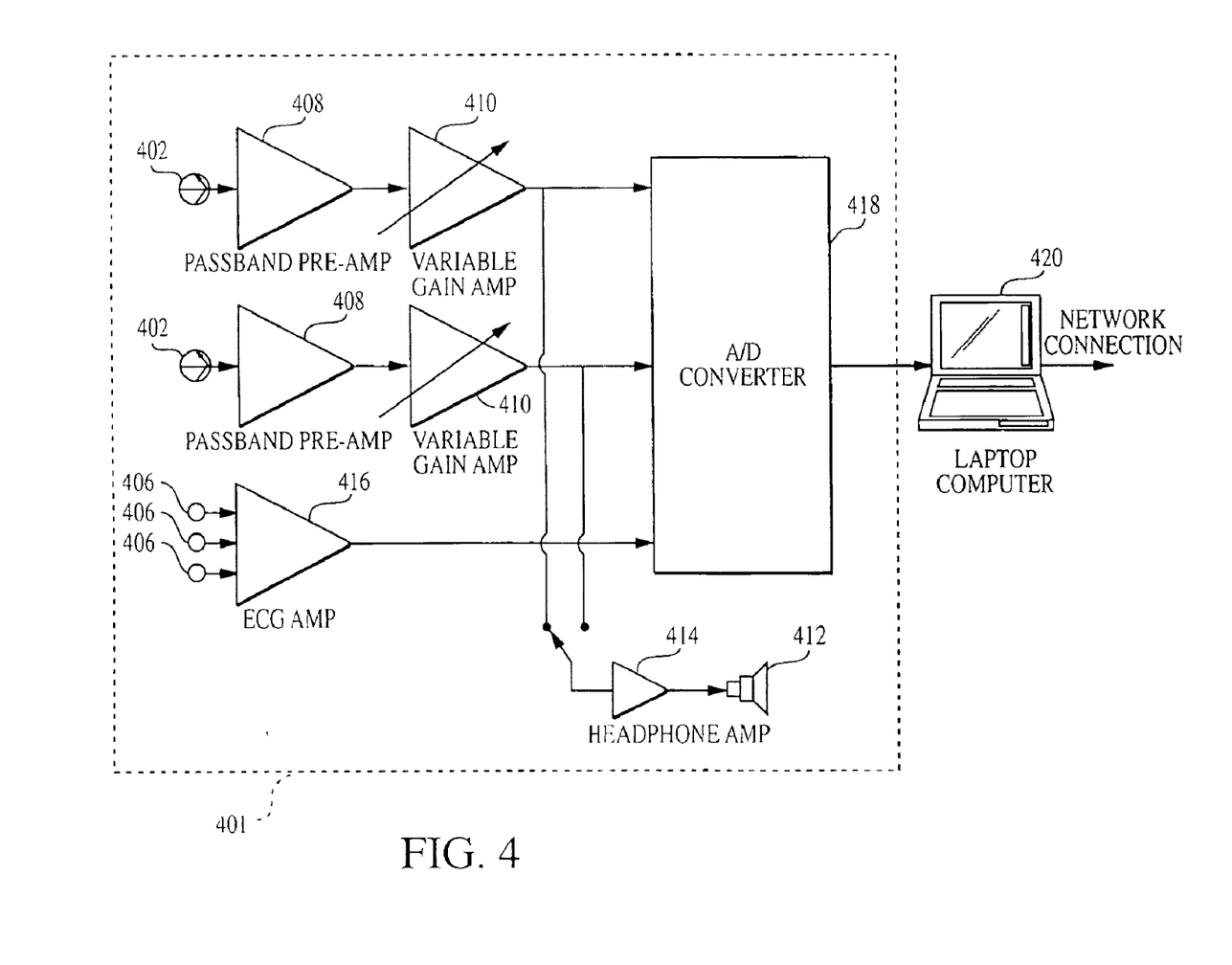
FIG. 4 illustrates a block diagram of system hardware.

A system block diagram of the present invention is illustrated in FIG. 4. The system is comprised of two principal elements. One is a patient data collection unit 401. The other is a computer processing device 420 including or having access to data storage devices. The patient data collection unit performs several functions including obtaining heart sound data via a set of contact microphones in the form of transducers. Two channels of acoustic data are obtained from a patient using a primary transducer 402 and a reference transducer 404. In addition, a set of ECG electrodes 406 are used to obtain electrocardiogram data from the patient.

The two contact microphones are each conditioned by a pre-amplifier 408 having a passband of 20 Hz to 2 kHz and variable gain amplification stage 410. A set of headphones 412 connected to a headphone amplifier 414 can be used to listen to the acoustic data gathered from the primary transducer 402 and the reference transducer 404. The ECG electrodes 406 feed into an ECG amplifier 416. Outputs from the variable gain amplifiers. 410 and the ECG amplifier 416 are fed to a analog-to-digital converter where the acoustic and ECG signals are digitized and recorded. A 12-bit National Instruments PCMCIA analog-to-digital converter is used, for instance, to collect and digitize data at a rate (e.g. 8.13 kHz) consistent with the highest data frequencies of interest.

Once the signals have been digitized and recorded, the patient data collection unit 401 forwards the data to a computer processing device 420. The computer processing device 420 is typically, a laptop computer (due to its compact transportable nature) having adequate data storage capacity. However, the patient data collection unit 401 may be connected to other computer processing devices without departing from the spirit or scope of the present invention. A computer software program accesses heart sound data that has either been collected and forwarded by the patient data collection unit 401, or is resident on the laptop computer 420, or can be obtained from another source of heart sound data. The computer program applies a screening algorithm to the heart sound data in order to determine whether the heart sound data is to be classified as normal or pathologic. Each heart sound data file corresponds to a different patient. When the algorithm has operated on the heart sound data that has been input, the computer program will display the results on a display screen to the doctor, nurse, or technician operating the computer. Results indicating a pathologic condition will likely cause the patient to be referred to a cardiologist for further examination. Otherwise, a cardiologist referral can be deemed unnecessary.

Figure 5:
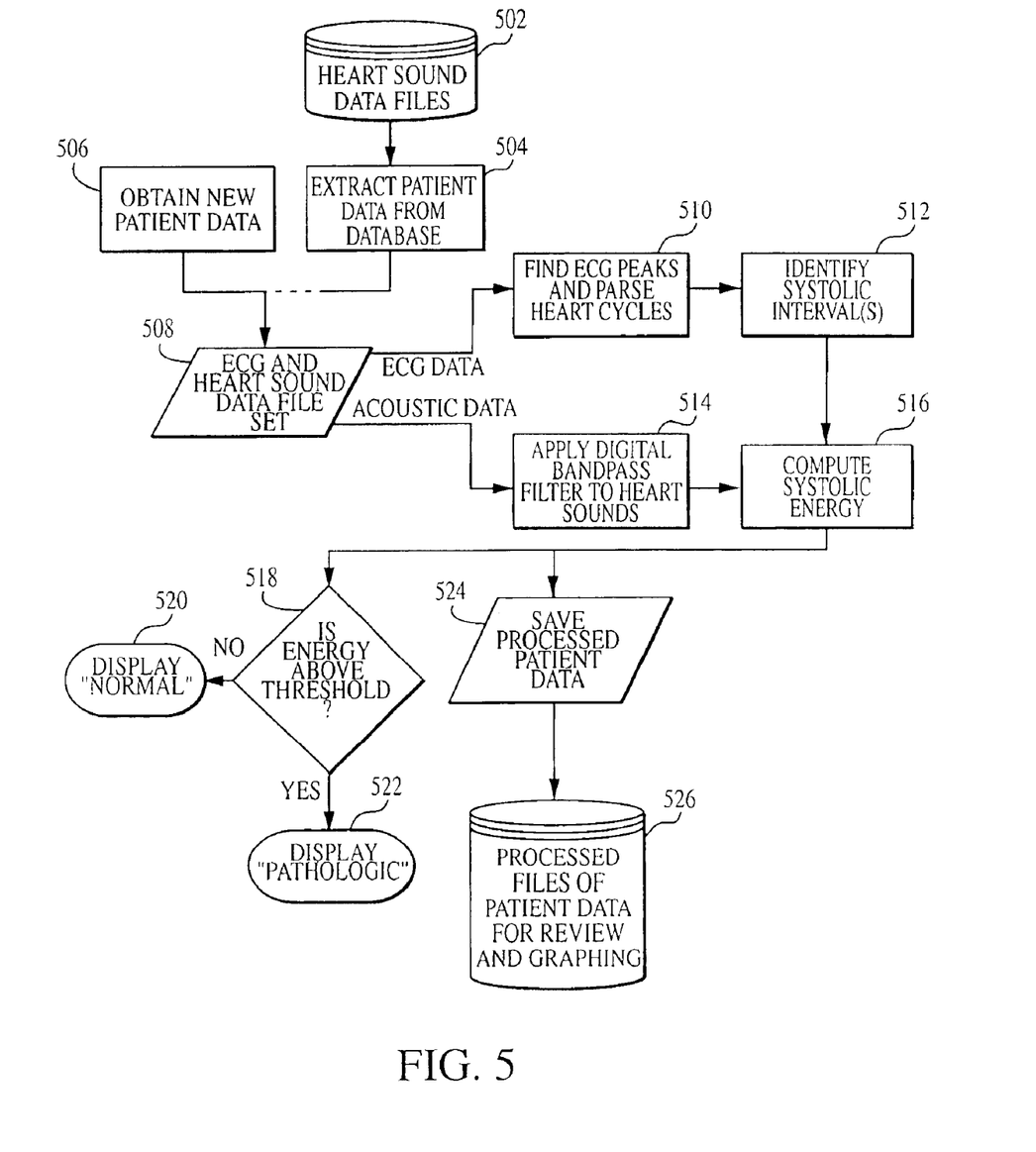
FIG. 5 illustrates a logic flow diagram of the processes used to diagnose pathologic heart conditions.

FIG. 5 illustrates the flow of logic and processing that occurs in the various elements described in FIG. 4. Digitized heart sound recordings were collected on patients in the Pediatric Cardiology Echocardiography Laboratory in the Johns Hopkins Outpatient Center. The recordings were stored in a Heart Sound database 502. Recorded heart sounds could then be extracted 504 from the heart sound database 502 and placed into an ECG/heart sound data file set 508. Alternatively, ECG and heart sound data could be obtained directly from a patient 506 and placed into the ECG/heart sound data file set 508. The ECG/heart sound data file set 508 serves as the data to be fed to a screening algorithm. The purpose of the screening algorithm is to analyze the ECG data and heart sound data in order to detect any pathologic anomalies that may be present. Thus the system is to be used as a diagnostic aid. In order for the screening algorithm to be applied, the data set must first be manipulated. Initially, the ECG data and acoustic heart sound data are separated. The ECG data is used to parse the time series into a sequence of individual heart cycles via a process that identifies the ECG peaks 510.

A systolic interval is then identified 512 for each heart cycle. The first and second heart sounds are identified either by reference to the heart cycle boundaries or acoustically using a passband of 25–140 Hz. In the acoustic method the times of the acoustic maxima define systole and diastole. Systole can then be divided into various sub-intervals including, but not limited to, the first half of the systolic interval, the total systolic interval, the middle half of the systolic interval, and the last half of the systolic interval, "beginning after S1 and ending at S2, as shown in FIG. 3 for a pan-systolic murmer." A short interval to isolate the first and second heart sounds is factored in. Meanwhile, the acoustic heart sound data is passed through a digital bandpass filter 514, in this case a second order coiflet CWT transform. Next, a relative energy value (square of the wavelet coefficient expressed in dB) for a given wavelet scale and systolic subinterval is calculated 516.

A composite relative energy value across all included heart cycles is computed. The composite energy value can be computed in several manners. One way is to compute it as the median of the set of computed energy values for each systolic sub-interval of the included heart cycles. A second way is to compute it as the weighted average of the set of computed energy values for each systolic sub-interval of the included heart cycles. A third way is to compute it as the median relative energy across more than one of the heart cycle systolic sub-intervals. A fourth way is to compute it as the weighted average relative energy value across more than one of the heart cycle systolic sub-intervals. Those of ordinary skill in the art could readily devise other alternative ways in which to compute a composite energy value without departing from the spirit or scope of the present invention. The specific methods described herein are illustrative and not intended to limit the invention to a particular manner for computing a composite energy value.

A decision 518 between healthy 520 and pathologic 522 hearts is made on the basis of the calculated composite relative energy value being above or below a certain threshold. A patient's processed data is saved 524 for optional further technical analysis, and added to a database 526. Among the various uses of the database 526 are reviewing and improving the algorithm's performance.

Figure 6:
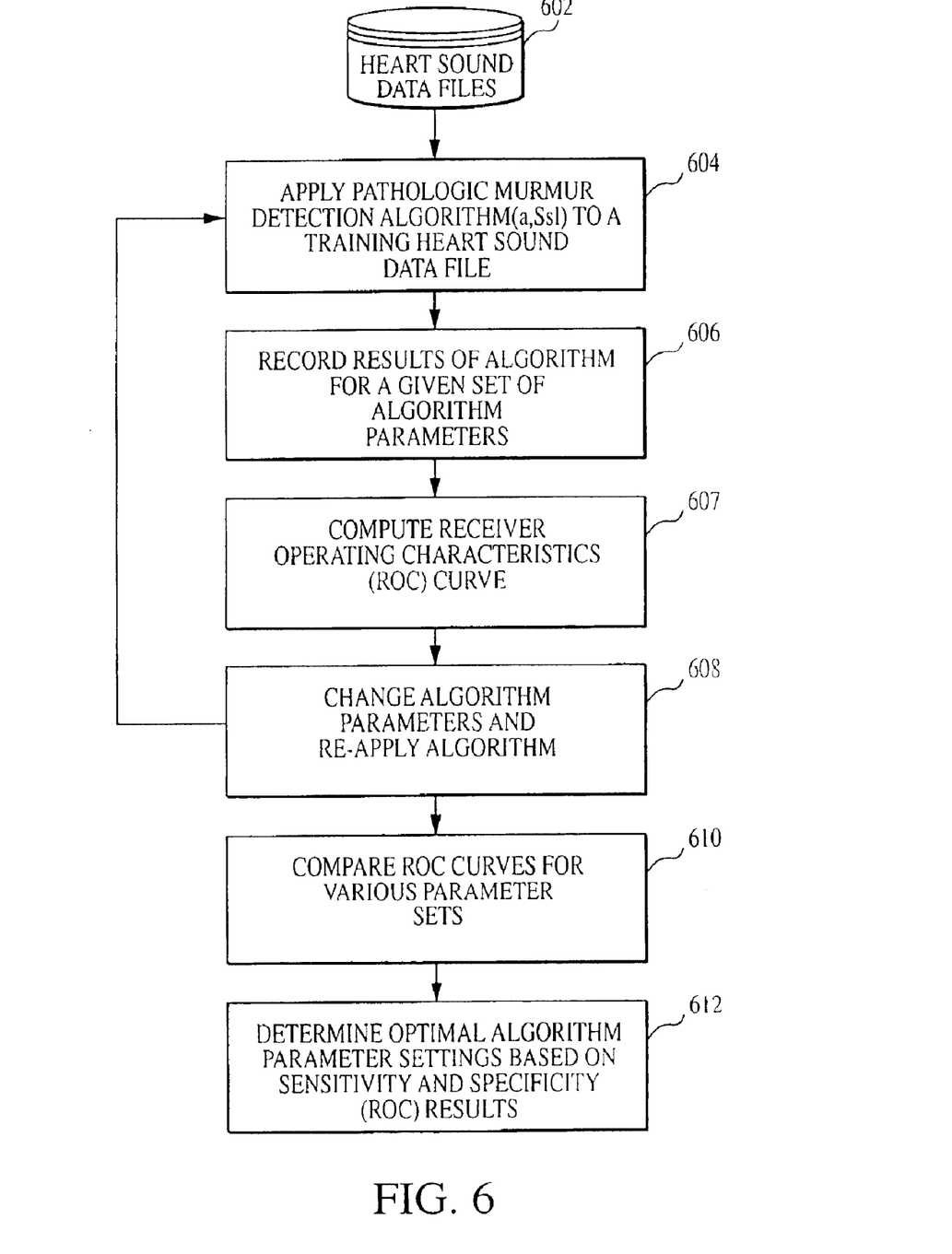
FIG. 6 illustrates a logic flow diagram for optimizing the parameters of a time-frequency screening algorithm.

FIG. 6 illustrates a logic flow diagram for optimizing the parameters of a time-frequency screening algorithm. The diagnostic system and processes described above were applied to a set of heart sounds. A set of known pathologic heart sounds and a set of known normal heart sounds taken in the first half of each month over a period of time were extracted from the heart sound database 602. Files from the latter half of the months were preserved as "new" data to test algorithm performance after algorithm tuning. Each heart sound data file corresponds to a different patient. The screening algorithm is applied 604 to a patient's heart sound data file and the results are recorded 606. Performance of the screening algorithm over all tested patients for a given threshold was measured by the ratio of called positives to true positives, within a universe of known positives (the "sensitivity"), paired with the ratio of called negatives to true negatives, within a universe of known negatives (the "specificity"). Sensitivity vs. specificity curves for a variety of thresholds and systolic intervals were plotted 607. These curves are called "Receiver Operating Characteristic" or "ROC" curves.

The test is then repeated 608 on the same heart sound data using a different set of wavelet parameters, specifically, the scale ($\alpha$) and the systolic sub-interval (SsI) are varied. This is done for numerous combinations of scale and systolic sub-interval. Once the heart sound data for all patients has been subjected to the screening algorithm and results have been recorded for the numerous scale and systolic sub-interval variations, the program compares the ROC curves for each wavelet scale/systolic sub-interval combination 610. The area beneath each ROC curve is computed and the ROC curve having an area closest to "1" is deemed to have the best results. The parameters for that ROC curve are then chosen as the optimal parameters to use with the screening algorithm 612.

The ROC curves, in the test case, indicated that the most optimal algorithm settings used a wavelet scale, $\alpha$, of 16 and was applied to the middle half systolic sub-interval. The best results were typically obtained using a systolic interval centered on systole meaning that the midpoint of the systolic interval and the midpoint of the systolic sub-interval are the same. Those of ordinary skill in the art could readily adjust the algorithm for different wavelet scales and systolic sub-intervals without departing from the spirit or scope of the present invention.

Using these optimum parameters, the algorithm was then applied to an expanded data set that included both half months plus additional data collected while the previously described analysis was in progress. Of 143 cases tested, 95 were from normal hearts (with and without innocent murmurs) and 48 were from hearts with pathology (i.e., murmur grade $\geq 2$). Sensitivity and specificity ratios of 96% were achieved.

There are several advantages realized by the present invention. An automatic screening algorithm would be useful for detecting pathologic heart murmurs in settings where a trained professional is not always available, such as pre sports participation physicals, and examinations performed in remote or underserved areas. Furthermore, automated analysis of digitized clinical information such as heart sounds could have major implications for health care delivery systems using telemedicine.

Automated analysis of heart sound data could also be used by cardiologists to quantitatively follow and document changes in severity of certain conditions such as aortic stenosis and mitral regurgitation, in which changes in murmur characteristics are known to correlate with changes in disease severity. In addition, since data for analysis could theoretically be collected using any electronic stethoscope, home care nurses or nurses aides could make inexpensive in-home bedside recordings that could be analyzed later to monitor changes in certain conditions as reflected in heart sounds.

It is to be understood that the present invention illustrated herein is readily implementable by those of ordinary skill in the art as a computer program product having a medium with computer program(s) embodied thereon. The computer program product is capable of being loaded and executed on the appropriate computer processing device(s) in order to carry out the method or process steps described. Appropriate computer program code in combination with hardware implements many of the elements of the present invention.

This computer code is typically stored on removable storage media. This removable storage media includes, but is not limited to, a diskette, standard CD, pocket CD, zip disk, or mini zip disk. Additionally, the computer program code can be transferred to the appropriate hardware over some type of data network.

The present invention has been described, in part, with reference to flowcharts or logic flow diagrams. It will be understood that each block of the flowchart diagrams or logic flow diagrams, and combinations of blocks in the flowchart diagrams or logic flow diagrams, can be implemented by computer program instructions.

These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks or logic flow diagrams.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart blocks or logic flow diagrams. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart blocks or logic flow diagrams.

Accordingly, block(s) of flowchart diagrams and/or logic flow diagrams support combinations of means for performing the specified functions, combinations of steps for performing the specified functions and program instruction means for performing the specified functions. It will also be understood that each block of flowchart diagrams and/or logic flow diagrams, and combinations of blocks in flowchart diagrams and/or logic flow diagrams can be implemented by special purpose hardware-based computer systems that perform the specified functions or steps, or combinations of special purpose hardware and computer instructions.

In the following claims, any means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method of diagnosing pathologic heart conditions comprising:
   identifying a systolic sub-interval of a systolic interval for a plurality of heart cycles in a sequence of heart cycles;
   computing an energy value for each systolic sub-interval;
   computing a composite energy value using the computed energy values for each systolic sub-interval; and
   comparing the composite energy value to a threshold level in order to distinguish between a normal heart and a pathologic heart.

2. A method of diagnosing pathologic heart conditions comprising:
   filtering a time series of heart sounds;
   parsing the time series of heart sounds into a sequence of individual heart cycles;
   identifying a systolic interval for each heart cycle;
   identifying a systolic sub-interval of the systolic interval for each heart cycle;
   computing an energy value for the systolic sub-interval of one or more heart cycles, said energy value being proportional to the energy level associated with the filtered series of heart sounds;
   computing a composite energy value for the systolic sub-intervals of one or more heart cycles; and
   comparing the composite energy value to a threshold level in order to distinguish between a normal heart and a pathologic heart.

3. The method of claim 2 wherein said parsing step uses electro-cardiogram (ECG) data in order to transform a time series of heart sounds into a sequence of individual heart cycles.

4. The method of claim 2 wherein said parsing step uses acoustic heart sounds obtained directly from a patient in order to transform a time series of heart sounds into a sequence of individual heart cycles.

5. The method of claim 2 wherein identifying a systolic interval for each heart cycle is achieved by identifying pulses on an electro-cardiogram (ECG).

6. The method of claim 2 wherein identifying a systolic interval for each heart cycle is achieved by acoustically locating a first and a second heart sound using a bandpass filter, said bandpass filter applied to the time series of heart sounds.

7. The method of claim 2 wherein filtering the time series of heart sounds is achieved using a bandpass filter.

8. The method of claim 2 wherein filtering the time series of heart sounds is achieved using time-frequency transforms.

9. The method of claim 8 wherein the time-frequency transform is a wavelet transform.

10. The method of claim 8 wherein the time-frequency transform is a Fourier transform.

11. The method of claim 2 wherein the systolic sub-interval is centered in systole.

12. The method of claim 2 wherein the systolic sub-interval is centered in systole and is half of the systolic interval.

13. The method of claim 2 wherein the composite energy value is computed as the median of the computed energy values for more than one of the systolic sub-intervals of the heart cycles.

14. The method of claim 2 wherein the composite energy value is computed as the weighted average of more than one of the computed energy values for the systolic sub-intervals of the heart cycles.

15. The method of claim 2 wherein the composite energy value is computed as the median across more than one of the heart cycle systolic sub-intervals of a quantity proportional to energy.

16. The method of claim 2 wherein the composite energy value is computed as the weighted average energy value across more than one of the heart cycle systolic sub-intervals.

17. The method of claim 14 wherein the ratio of energies between systolic interval and diastolic interval are also used to distinguish a normal heart from a pathologic heart by prior statistical characterization of the ratio of energies between systolic interval and diastolic interval for normal and pathologic hearts.

18. The method of claim 14 wherein the standard deviation of the energy in a systolic interval is also used to distinguish a normal heart from a pathologic heart by prior statistical characterization of the standard deviation of the energy in a systolic interval for normal and pathologic hearts.

19. A system for diagnosing pathologic heart conditions comprising:
  a portable computing device for:
    managing data collection from new patients;
    storing data; and
    analyzing data,
  and
  a patient data collection unit for acquiring electro-cardiogram (ECG) and heart sound data from a patient, said patient data collection unit operatively connected with said portable computing device, wherein the patient data collection unit comprises:
  a contact microphone for obtaining acoustic data;
  an acoustic pre-amplifier operatively connected with said contact microphone, said pre-amplifier having a pass-band of 20 Hz to 2 kHz used to condition acoustic data received from said contact microphone;
  a variable amplifier operatively connected with said acoustic pre-amplifier for variably amplifying the conditioned acoustic data;
  an electro-cardiogram (ECG) electrode;
  an ECG amplifier operatively connected with said electro-cardiogram (ECG) electrode;
  an analog to digital converter operatively connected with said variable amplifier and said ECG amplifier, said analog to digital converter for digitizing acoustic data and electro-cardiogram (ECG) data.

20. A method of optimizing a heart auscultation screening algorithm comprising:
  applying a heart auscultation screening time-frequency transform algorithm to a set of data, wherein:
    said algorithm includes wavelets and bandpass filters;
    said data includes heart sounds known to be normal and heart sounds known to be pathologic;
    said heart sounds being characterized by a systolic interval;
    said systolic interval capable of being divided into systolic sub-intervals,
  recording the results of said heart auscultation screening algorithm for a variety of time-frequency transform parameters and systolic sub-intervals; and
  determining an optimal combination of wavelet scale parameter and systolic sub-interval for use with said heart auscultation screening wavelet algorithm based on sensitivity and specificity measurements.

21. A computer readable medium whose contents cause a computer based system to determine patient heart pathology by:
  identifying a systolic sub-interval of a systolic interval for a plurality of heart cycles in a sequence of heart cycles;
  computing an energy value for each systolic sub-interval;
  computing a composite energy value using the computed energy values for each systolic sub-interval; and
  comparing the composite energy value to a threshold level in order to distinguish between a normal heart and a pathologic heart.

22. A computer readable medium whose contents cause a computer based system to determine patient heart pathology by:
  filtering a time series of heart sounds;
  parsing the time series of heart sounds into a sequence of individual heart cycles;
  identifying a systolic interval for each heart cycle;
  identifying a systolic sub-interval of the systolic interval for each heart cycle;
  computing an energy value for the systolic sub-interval of one or more heart cycles, said energy value being proportional to the energy level associated with the filtered series of heart sounds;
  computing a composite energy value for the systolic sub-intervals of one or more heart cycles; and
  comparing the composite energy value to a threshold level in order to distinguish between a normal heart and a pathologic heart.

23. A computer readable medium whose contents transform a computer based system into a heart pathology detection system, comprising:
  a patient data collection subsystem for acquiring electro-cardiogram (ECG) and heart sound data from a patient;
  a data management subsystem for managing electro-cardiogram (ECG) and heart sound data;
  a data analysis subsystem for processing and analyzing electro-cardiogram (ECG) and heart sound data comprising:
    means for identifying a systolic sub-interval of a systolic interval for a plurality of heart cycles in a sequence of heart cycles;
    means for computing an energy value for each systolic sub-interval;
    means for computing a composite energy value using the computed energy values for each systolic sub-interval; and
    means for comparing the composite energy value to a threshold level in order to distinguish between a normal heart and a pathologic heart; and
  a data storage subsystem for storing processed electro-cardiogram (ECG) and heart sound data.

* * * * *